United States Patent
Deborski et al.

(10) Patent No.: US 9,113,897 B2
(45) Date of Patent: Aug. 25, 2015

(54) PARTITIONED SURGICAL INSTRUMENT

(71) Applicant: Covidien LP, Mansfield, MA (US)

(72) Inventors: Christopher A. Deborski, Denver, CO (US); Russell D. Hempstead, Lafayette, CO (US); Keir Hart, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 279 days.

(21) Appl. No.: 13/741,550

(22) Filed: Jan. 15, 2013

(65) Prior Publication Data

US 2013/0190755 A1  Jul. 25, 2013

Related U.S. Application Data

(60) Provisional application No. 61/589,549, filed on Jan. 23, 2012.

(51) Int. Cl.
*A61B 18/12* (2006.01)
*A61B 18/14* (2006.01)
*A61B 17/00* (2006.01)

(52) U.S. Cl.
CPC .............. *A61B 18/14* (2013.01); *A61B 18/1445* (2013.01); *A61B 2017/0046* (2013.01); *A61B 2018/1455* (2013.01); *A61B 2018/1495* (2013.01)

(58) Field of Classification Search
CPC ........... A61B 18/1445; A61B 18/1442; A61B 2017/0046; A61B 2018/1445; A61B 2018/1495
USPC ....................................... 606/51–52
See application file for complete search history.

(56) References Cited

U.S. PATENT DOCUMENTS 2,541,246 A * 2/1951 Held .............................. 606/205
D249,549 S 9/1978 Pike
D263,020 S 2/1982 Rau, III
(Continued)

FOREIGN PATENT DOCUMENTS

CN 201299462 9/2009
DE 2415263 10/1975
(Continued)

OTHER PUBLICATIONS

European Search Report No. EP13152331.8 dated May 15, 2013.
(Continued)

*Primary Examiner* — Michael Peffley
*Assistant Examiner* — Daniel Fowler

(57) ABSTRACT

A surgical instrument a reusable component and a disposable component selectively separable from and engagable with the reusable component. The disposable component includes an end effector and a mechanical actuator operable to induce mechanical movement of the end effector. The reusable component is configured for providing electrosurgical energy to the disposable component when engaged with the disposable component. A physical mating feature is configured to maintain engagement between the reusable and disposable components when the reusable and disposable components are engaged, and an electrical mating feature is configured to transmit electrical energy between the disposable and reusable components when the disposable and reusable components are engaged. All mechanical motion resulting from operation of the mechanical actuator may be contained within the disposable component.

19 Claims, 4 Drawing Sheets

(56) References Cited

U.S. PATENT DOCUMENTS

| | | |
|---|---|---|
| 4,733,662 A | 3/1988 | DeSatnick et al. |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 4,936,842 A | 6/1990 | D'Amelio et al. |
| 5,217,477 A | 6/1993 | Lager |
| D343,453 S | 1/1994 | Noda |
| 5,281,220 A * | 1/1994 | Blake, III ............... 606/46 |
| 5,282,800 A | 2/1994 | Foshee et al. |
| D348,930 S | 7/1994 | Olson |
| D349,341 S | 8/1994 | Lichtman et al. |
| 5,366,476 A * | 11/1994 | Noda ............... 606/206 |
| D354,564 S | 1/1995 | Medema |
| 5,391,166 A | 2/1995 | Eggers |
| 5,396,900 A * | 3/1995 | Slater et al. ............... 600/564 |
| D358,887 S | 5/1995 | Feinberg |
| 5,520,702 A | 5/1996 | Sauer et al. |
| 5,564,615 A | 10/1996 | Bishop et al. |
| D384,413 S | 9/1997 | Zlock et al. |
| 5,665,085 A * | 9/1997 | Nardella ............... 606/41 |
| H1745 H | 8/1998 | Paraschac |
| 5,814,043 A | 9/1998 | Shapeton |
| D402,028 S | 12/1998 | Grimm et al. |
| D408,018 S | 4/1999 | McNaughton |
| 5,913,874 A | 6/1999 | Berns et al. |
| 5,947,964 A * | 9/1999 | Eggers et al. ............... 606/41 |
| D416,089 S | 11/1999 | Barton et al. |
| D424,694 S | 5/2000 | Tetzlaff et al. |
| D425,201 S | 5/2000 | Tetzlaff et al. |
| 6,059,776 A | 5/2000 | Gatto |
| H1904 H | 10/2000 | Yates et al. |
| 6,183,467 B1 | 2/2001 | Shapeton et al. |
| D449,886 S | 10/2001 | Tetzlaff et al. |
| D453,923 S | 2/2002 | Olson |
| D454,951 S | 3/2002 | Bon |
| 6,358,249 B1 * | 3/2002 | Chen et al. ............... 606/45 |
| 6,358,268 B1 | 3/2002 | Hunt et al. |
| D457,958 S | 5/2002 | Dycus et al. |
| D457,959 S | 5/2002 | Tetzlaff et al. |
| H2037 H | 7/2002 | Yates et al. |
| 6,425,896 B1 * | 7/2002 | Baltschun et al. ............... 606/51 |
| 6,458,130 B1 * | 10/2002 | Frazier et al. ............... 606/51 |
| D465,281 S | 11/2002 | Lang |
| D466,209 S | 11/2002 | Bon |
| D493,888 S | 8/2004 | Reschke |
| 6,773,409 B2 | 8/2004 | Truckai et al. |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| 7,131,970 B2 | 11/2006 | Moses et al. |
| D533,274 S | 12/2006 | Visconti et al. |
| D533,942 S | 12/2006 | Kerr et al. |
| D535,027 S | 1/2007 | James et al. |
| 7,160,298 B2 | 1/2007 | Lawes et al. |
| D538,932 S | 3/2007 | Malik |
| D541,418 S | 4/2007 | Schechter et al. |
| 7,204,832 B2 | 4/2007 | Altshuler et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| 7,270,664 B2 | 9/2007 | Johnson et al. |
| 7,276,068 B2 | 10/2007 | Johnson et al. |
| 7,318,823 B2 | 1/2008 | Sharps et al. |
| D564,662 S | 3/2008 | Moses et al. |
| 7,347,864 B2 | 3/2008 | Vargas |
| D567,943 S | 4/2008 | Moses et al. |
| 7,377,920 B2 | 5/2008 | Buysse et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,766,910 B2 | 8/2010 | Hixson et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,951,149 B2 | 5/2011 | Carlton |
| 7,955,331 B2 | 6/2011 | Truckai et al. |
| D649,249 S | 11/2011 | Guerra |
| D649,643 S | 11/2011 | Allen, IV et al. |
| 8,133,224 B2 | 3/2012 | Geiselhart |
| 8,133,254 B2 | 3/2012 | Dumbauld et al. |
| 8,142,474 B2 | 3/2012 | Hafner |
| 8,157,145 B2 | 4/2012 | Shelton, IV et al. |
| 8,162,940 B2 | 4/2012 | Johnson et al. |
| D661,394 S | 6/2012 | Romero et al. |
| 8,298,232 B2 | 10/2012 | Unger |
| 8,333,765 B2 | 12/2012 | Johnson et al. |
| 2009/0125027 A1 * | 5/2009 | Fischer ............... 606/46 |
| 2010/0145334 A1 * | 6/2010 | Olson et al. ............... 606/48 |
| 2011/0319888 A1 | 12/2011 | Mueller et al. |
| 2012/0221004 A1 | 8/2012 | Kerr |
| 2012/0226275 A1 | 9/2012 | Allen, IV |
| 2012/0226276 A1 | 9/2012 | Dycus |
| 2012/0239034 A1 | 9/2012 | Horner |
| 2012/0253344 A1 | 10/2012 | Dumbauld |
| 2012/0259331 A1 | 10/2012 | Garrison |
| 2012/0265241 A1 | 10/2012 | Hart |
| 2012/0271346 A1 | 10/2012 | Townsend |
| 2012/0283727 A1 | 11/2012 | Twomey |
| 2012/0283729 A1 | 11/2012 | Kappus |
| 2012/0283734 A1 | 11/2012 | Ourada |
| 2012/0296205 A1 | 11/2012 | Chernov |
| 2012/0296238 A1 | 11/2012 | Chernov |
| 2012/0296239 A1 | 11/2012 | Chernov |
| 2012/0296317 A1 | 11/2012 | Chernov |
| 2012/0296323 A1 | 11/2012 | Chernov |
| 2012/0296324 A1 | 11/2012 | Chernov |
| 2012/0296332 A1 | 11/2012 | Chernov |
| 2012/0296333 A1 | 11/2012 | Twomey |
| 2012/0296334 A1 | 11/2012 | Kharin |
| 2012/0296371 A1 | 11/2012 | Kappus |
| 2012/0303021 A1 | 11/2012 | Guerra |
| 2012/0303023 A1 | 11/2012 | Bucciaglia |
| 2012/0303025 A1 | 11/2012 | Garrison |
| 2012/0303026 A1 | 11/2012 | Dycus |
| 2012/0310240 A1 | 12/2012 | Olson |
| 2012/0316601 A1 | 12/2012 | Twomey |
| 2012/0323238 A1 | 12/2012 | Tyrrell |
| 2012/0330308 A1 | 12/2012 | Joseph |
| 2012/0330309 A1 | 12/2012 | Joseph |
| 2013/0014375 A1 | 1/2013 | Hempstead |
| 2013/0018364 A1 | 1/2013 | Chernov |
| 2013/0018371 A1 | 1/2013 | Twomey |
| 2013/0018372 A1 | 1/2013 | Sims |
| 2013/0018411 A1 | 1/2013 | Collings |
| 2013/0022495 A1 | 1/2013 | Allen, IV |
| 2013/0041370 A1 | 2/2013 | Unger |
| 2013/0041402 A1 | 2/2013 | Chojin |
| 2013/0046295 A1 | 2/2013 | Kerr |
| 2013/0046303 A1 | 2/2013 | Evans |
| 2013/0046306 A1 | 2/2013 | Evans |
| 2013/0046337 A1 | 2/2013 | Evans |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |

(56) References Cited

FOREIGN PATENT DOCUMENTS

| | | |
|---|---|---|
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 0 947 167 | 6/1999 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-000538 | 1/1997 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-152663 | 6/2005 |
| JP | 2005-253789 | 9/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 94/08524 | 4/1994 |
| WO | WO 95/07662 | 3/1995 |
| WO | WO 98/57603 | 12/1998 |
| WO | WO 00/36986 | 6/2000 |
| WO | WO 00/59392 | 10/2000 |
| WO | WO 00/66014 | 11/2000 |
| WO | WO 01/01847 | 1/2001 |
| WO | WO 01/15614 | 3/2001 |
| WO | WO 01/54604 | 8/2001 |
| WO | WO 02/045589 | 6/2002 |
| WO | WO 2005/110264 | 11/2005 |
| WO | WO 2006/021269 | 3/2006 |
| WO | WO 2008/040483 | 4/2008 |

OTHER PUBLICATIONS

U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 13/223,521, filed Sep. 1, 2011, John R. Twomey.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/360,925, filed Jan. 30, 2012, James H. Orszulak.
U.S. Appl. No. 13/400,290, filed Feb. 20, 2012, Eric R. Larson.
U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium,

(56) References Cited

OTHER PUBLICATIONS and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.

\* cited by examiner

PARTITIONED SURGICAL INSTRUMENT

CROSS REFERENCE TO RELATED APPLICATION

This application claims priority to and the benefit of U.S. Provisional Application Ser. No. 61/589,549 entitled "PARTITIONED SURGICAL INSTRUMENT" filed Jan. 23, 2012 by Christopher A. Deborski et al., the entire contents of which being incorporated by reference herein.

BACKGROUND

1. Technical Field

The present disclosure relates generally the field of reposable or reusable surgical instruments. In particular, the disclosure relates to instruments having separable and replaceable components to provide clean, sterile or refurbished surfaces in each instance of use.

2. Background of Related Art

Instruments such as electrosurgical forceps are commonly used in open and endoscopic surgical procedures to coagulate, cauterize and seal tissue. Such forceps typically include a pair of jaw members that can be controlled by a surgeon to grasp targeted tissue, such as, e.g., a blood vessel. The jaw members may be approximated to apply a mechanical clamping force to the tissue, and are associated with at least one electrode surface to permit the delivery of electrosurgical energy to the tissue. The combination of the mechanical clamping force and the electrosurgical energy has been demonstrated to join adjacent layers of tissue captured between the jaw members. When the adjacent layers of tissue include the walls of a blood vessel, sealing the tissue may result in hemostasis. Thereafter, the sealed tissue may be transected by advancing a knife through the jaws. A detailed description of the use of an electrosurgical forceps may be found in U.S. Pat. No. 7,255,697 to Dycus et al.

In use, various tissue-contacting components of an electrosurgical forceps tend to become contaminated or degraded. For example, electrodes may become contaminated as portions of the treated tissue adhere to the tissue-contacting surfaces of the electrodes. Also, a knife blade may become dull and less effective in transecting sealed tissue after repeated use, even in a single surgical procedure. In order to provide clean electrodes and a sharp knife for a particular surgical procedure, a brand new instrument is often used. Once the procedure is complete, the used instrument is discarded.

Instruments that are reposable, or reusable for multiple procedures, reduce the instrumentation costs per procedure. Providing a reusable electrosurgical forceps, however, presents various challenges. For example, the complexity of an electrosurgical forceps tends to result in fairly labor intensive cleaning procedures to prepare the forceps for subsequent use. Improper cleaning may result in dangerous contamination being introduced to the surgical site. Also, some reusable forceps have removable and replaceable components to provide clean surfaces for each use. Many of these instruments require arduous disassembly and reassembly procedures that require extensive training, and may discourage use of the instrument.

SUMMARY

The present disclosure describes a surgical instrument for treating tissue. The surgical instrument includes a reusable component and a disposable component selectively separable from and engagable with the reusable component. The disposable component includes an end effector and a mechanical actuator operable to induce mechanical movement of the end effector. The reusable component is configured for providing electrosurgical energy to the disposable component when engaged with the disposable component. A physical mating feature is configured to maintain engagement between the reusable and disposable components when the reusable and disposable components are engaged, and an electrical mating feature is configured to transmit electrical energy between the disposable and reusable components when the disposable and reusable components are engaged. All mechanical motion resulting from operation of the mechanical actuator may be contained within the disposable component. By appropriately partitioning the instrument between relatively expensive electronic components and relatively inexpensive mechanical components, the cost per use of the instrument may be managed.

In one aspect of the present invention, the physical mating feature includes a pair of contoured guide arms disposed on the reusable component shaped to correspondingly mate with a pair of lateral indentations disposed on the disposable component. The contoured guide arms may include a plurality of bosses disposed on an interior surface thereof that are positioned to mate with corresponding cavities defined within the lateral indentations of the disposable component.

In another aspect of the present disclosure, the physical mating features on the reusable and disposable components may include lip and spring-loaded pin arrangements, tab and insert pins, screw or key features, magnetic and ferromagnetic components, adhesives or the like. The electrical mating feature may include a plurality of pins that extend from the reusable component that mate with a corresponding plurality of sockets defined in the housing of the disposable component. A contact guide may be disposed the reusable or disposable component and be configured to facilitate alignment and engagement of the plurality of pins and corresponding plurality of sockets.

In another aspect of the present disclosure, the electrical mating feature may include one or more spring contacts, ring or spade terminals and blade connectors disposed on the reusable and disposable components that are configured to provide electrical communication between components once engaged. A key-like interface may be utilized to maintain mechanical and/or electrical engagement between the reusable and disposable components during use thereof. The key-like interface may be configured to provide indication to one of the reusable or disposable components that the reusable and disposable components are properly engaged. Proper engagement therebetween may be a pre-requisite for initiation of electrical energy and a generator (or a control module associated with the generator) may be dependent upon this feedback as a safety precaution.

In yet another aspect of the present disclosure, the reusable component is configured to electrically and mechanically connect to an electrosurgical energy source through a cable connector having one or more prongs and a terminal array. The terminal array is configured to couple electrical signal transmission pathways associated with the reusable component to the electrosurgical energy source.

The present disclosure also relates to a surgical instrument including a disposable component having an end effector and a mechanical actuator disposed thereon, the mechanical actuator operable to induce mechanical movement of the end effector. A reusable component is included that is selectively separable from and engagable with the disposable component and includes an electrical switch disposed thereon configured to allow selective application of electrosurgical energy to the end effector when the reusable component is engaged with the disposable component. One or more physical mating features and one or more electrical mating features are provided on the reusable component each configured to engage the disposable component to maintain mechanical and electrical engagement therewith.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
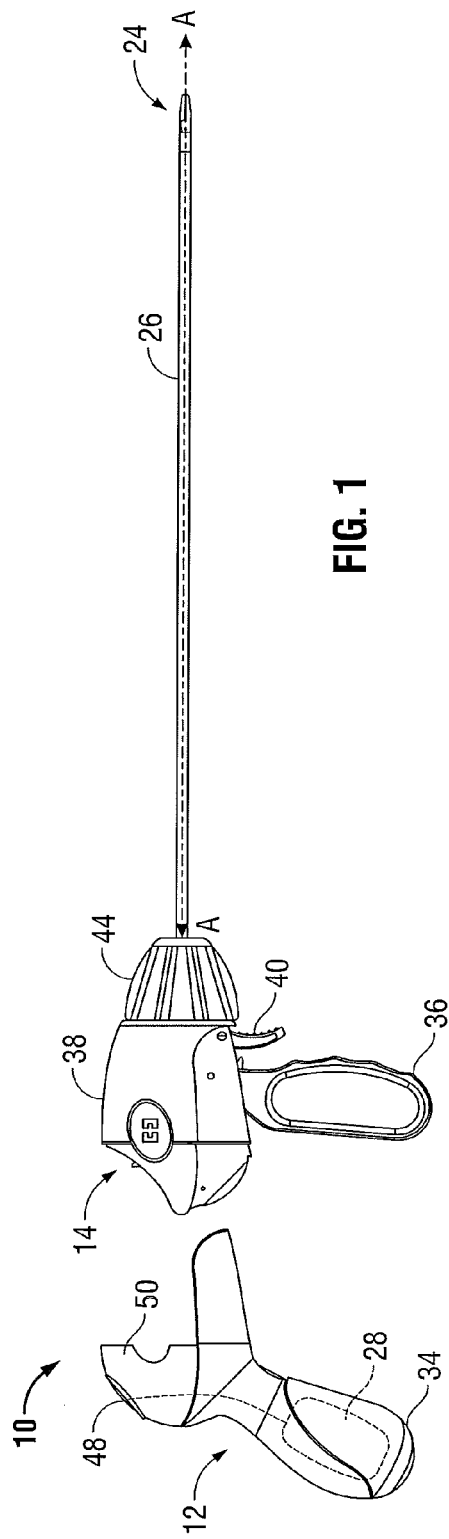
FIG. 1 is a right side view of a surgical instrument in accordance with an embodiment of the present disclosure with reusable and disposable components separated.
Figure 2:
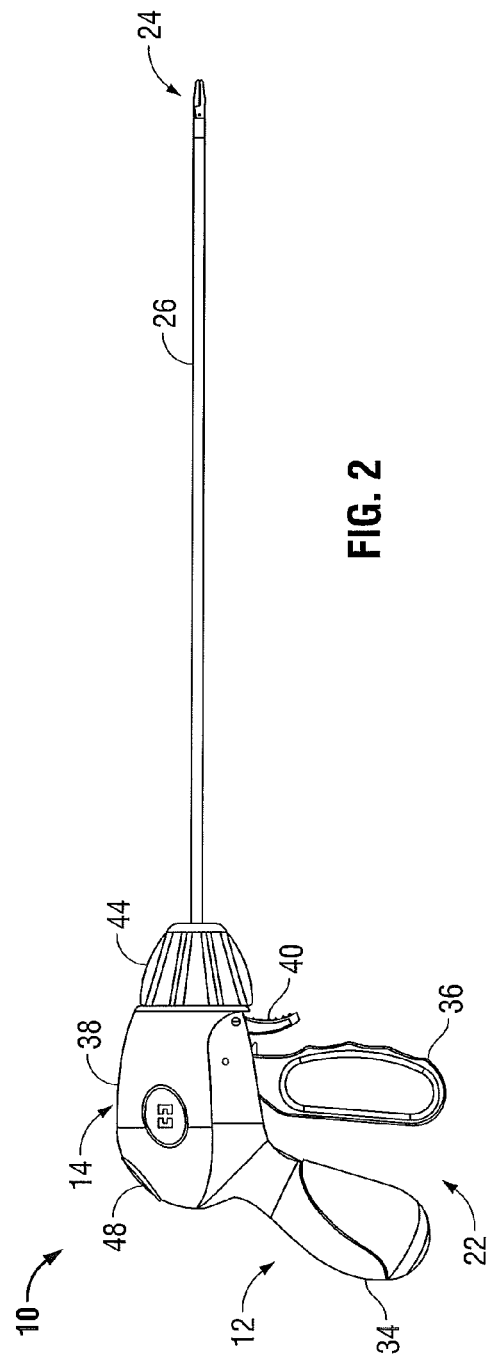
FIG. 2 is a right side view of the instrument of FIG. 1 with the components assembled.

Referring initially to FIGS. 1 and 2, an embodiment of an electrosurgical instrument 10 includes a reusable component 12 and a disposable component 14. The reusable component 12 and the disposable component 14 are selectively engagable with one another (FIG. 2) for use in a surgical procedure, and selectively removable from one another (FIG. 1) for disposal and/or refurbishment of the components 12, 14. The instrument 10 includes a handle assembly 22 at a proximal end thereof for remotely controlling an end effector 24 through an elongated shaft 26. Although this configuration is typically associated with instruments for use in laparoscopic or endoscopic surgical procedures, various aspects of the present disclosure are applicable to traditional open instruments, and in connection with endoluminal procedures as well.

The reusable component 12 of the instrument 10 includes a source of electrosurgical energy, e.g., an electrosurgical generator 28. When the reusable component 12 is coupled to the disposable component 14, the generator 28 selectively supplies electrosurgical energy to the end effector 24. Generators 28 such as the LIGASURE® Vessel Sealing Generator and the Force Triad® Generator as sold by Covidien of Boulder Colo. may be utilized for this purpose. The generator 28, depicted schematically in FIG. 1, may include a battery for supplying power to the instrument, electronic control mechanisms, electrical switching, cordage and other analog or digital devices. Thus, these relatively complex electronic devices required for electrically controlling the instrument 10 are housed within the reusable component 12, and may be used and reused for multiple surgical procedures.

To control the end effector 14, the handle assembly 12 includes a stationary handle 34 disposed on the reusable component 34 and a movable handle 36 disposed on the disposable component 14. The movable handle 36 is pivotable with respect to a housing 38 of the disposable component and, thus, the movable handle 36 is also pivotable with respect to the stationary handle 34 when the reusable and disposable components 12 and 14 are coupled to one another. The movable handle 36 is operatively coupled to the end effector 14 such that the movable handle 36 may be separated and approximated relative to the stationary handle 34 to respectively open and close the end effector 24. An elongated reciprocating drive element (not shown) is coupled to the movable handle 36, and reciprocates longitudinally through the elongated shaft 26 in response to pivoting of the movable handle 36.

A trigger 40 is also disposed on the disposable component 14, and is operable to extend and retract a knife (not shown) through the end effector 24. The trigger 24 is operatively coupled to a proximal end of a reciprocating knife drive element (not explicitly shown), and the knife is operatively coupled to a distal end of the knife drive element. Thus, the trigger 24 is pivotable relative to the housing 38 to longitudinally move the knife drive element through the elongated shaft 26, and the knife through the end effector 24. Also disposed on the disposable component 14 is a rotation knob 44. The rotation knob 44 is operable to rotate the elongated shaft 26 and the end effector 24 about a longitudinal axis A-A defined by the elongated shaft 26. The movable handle 36, knife actuation trigger 40 and rotation knob 44 may be collectively described as mechanical actuators since these features all cooperate to impart mechanical movement to the end effector 24. A detailed description of the use of a movable handle 36, knife actuation trigger 40 and rotation knob 44 as mechanical actuators may be found in U.S. Pat. No. 7,255, 697 to Dycus et al. In other embodiments (not shown) an electronic user interface in operative communication with the end effector 24 may be provided as a mechanical actuator.

The instrument 10 also includes an electrical actuator to permit electrical actuation of the instrument 10. The electrical actuator is configured as a button or switch 48, and is disposed on a housing 50 of the reusable component 12 of the instrument 10. The button 48 is in electrical communication with the generator 28. When the reusable component 12 and disposable component 14 are assembled, the button 48 is also in electrical communication with the end effector 24. The button 48 is thus operable to initiate and terminate the delivery of electrosurgical energy to the end effector 24. Other configurations or types of electrical actuators may be provided, such as an electrical switch disposed on the disposable component 14, a separate footswitch (not shown) or other user-manipulated implement.

After use, the reusable component 12 and button 48 are sterilizable by conventional sterilization techniques, such as autoclaving or gas sterilization using ethylene oxide or the like while the disposable component 14 is discarded. In this manner, a surgeon is able to utilize the same specifically-sized or custom-shaped reusable component 12 for multiple surgical procedures with different disposable components 14. Moreover, a surgeon may opt to interchange disposable components 14 during a particular procedure while at the same time utilizing the same reusable component 12. Feedback systems and sensors (not explicitly shown) may be employed to automatically update the generator 28 (or a control module associated with the generator 28) each time a new disposable component 14 is engaged with the reusable component 12 or the same disposable component is swapped during a particular surgical procedure. Techniques may be employed to insure that the disposable component is not used for a subsequent surgery.

Figure 3:
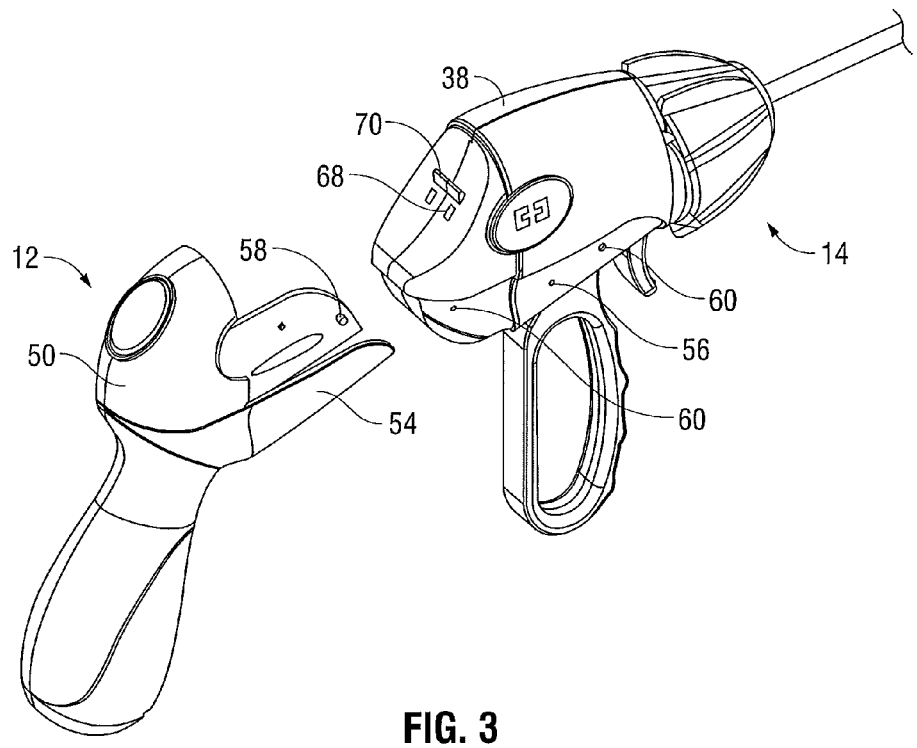
FIG. 3 is a partial, distally facing perspective view of the instrument of FIG. 1 with components separated, depicting electrical and physical mating features of the reusable component.
Figure 4:
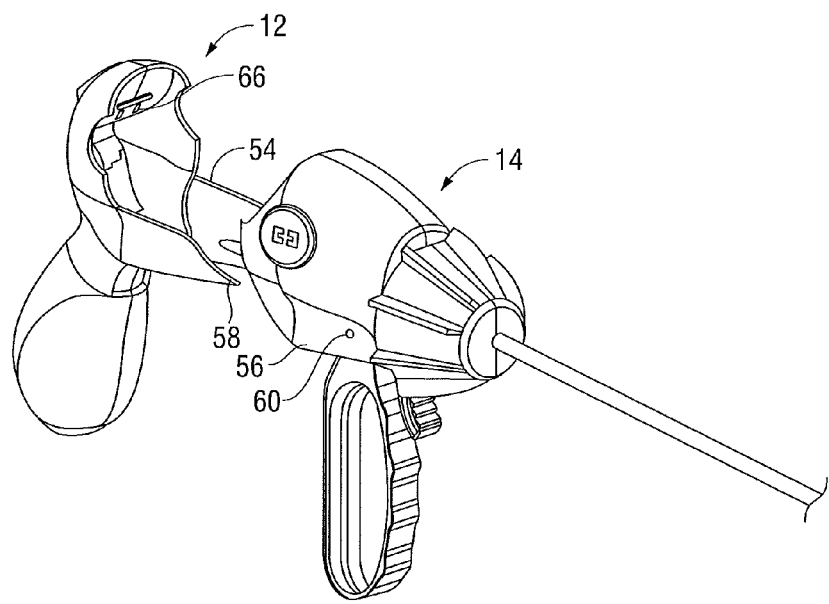
FIG. 4 is a partial, proximally facing perspective view of the instrument of FIG. 1 with components separated, depicting electrical and physical mating features of the disposable component.

Referring now to FIGS. 3 and 4, electrical and physical mating features permit the selective engagement and disengagement of the reusable and disposable components 12, 14 of the instrument 10. The physical mating features serve to secure and maintain the connection between the reusable and disposable components 12, 14, and the electrical mating features establish an electrical pathway between the two components 12, 14.

The physical mating features include a pair of contoured guide arms 54 on the reusable component 12 that are shaped to correspond to a pair of lateral indentations 56 on the disposable component 14. The guide arms 54 are received into the indentations 56 as the reusable and disposable components 12 and 14 are approximated, and facilitate alignment of the two components 12, 14. In one embodiment, a plurality of bosses 58 are provided on an interior or inner peripheral surface of the guide arms 54 that correspond to a plurality of cavities 60 provided in the indentation 56 of disposable component. The bosses 58 snap-fit into the cavities 60 to secure the disposable and reusable components, 14 and 12, to one another.

Other alternative physical or mechanical mating features are also contemplated including a lip and spring-loaded pin arrangement, a tab and inserted pins, a screw or key (see FIG. 5) that is separate or separable from reusable and disposable components 12, 14, or magnetic and ferromagnetic components may be provided to provide an attractive force between the two components 12, 14. Additionally, a cleanable adhesive could be provided on the disposable component 14, and a release strip could be removed to expose the adhesive prior to installation of the disposable component 14 to the reusable component 12.

The electrical mating features include a pair of pins 66 protruding from the housing 50 of reusable component 12 and a pair of corresponding sockets 68 defined in the housing 38 of the disposable component 14. Approximation of the reusable and disposable components 12, 14 effects electrical contact between the pins 66 and sockets 68 as the bosses 58 mechanically engage the cavities 60. A contact guide 70 is provided to facilitate alignment of the pins 66 with the corresponding sockets 68.

The pins 66 are in electrical communication with the generator 28 through the switch 48 (FIG. 1), and the sockets 70 are in electrical communication with the end effector 24 (FIG. 1). Thus, the generator 28 may provide RF therapeutic electrosurgical energy to the end effector 24 when the reusable and disposable components 12, 14 are engaged. The electrical mating features may alternatively or additionally include other types of electrical interfaces such as spring contacts, ring or spade terminals, or blade connectors. Also, any number of electrical mating features may be provided to accommodate any number of electrical signal transmission pathways between the reusable and disposable components 12, 14. Electrical pathways may be provided to transmit digital or analog signals, or to provide electrical power to any powered devices on the instrument disposable component 14. In some embodiments (see, e.g., FIG. 6, and related description below), the electrical pathways may extend to a connector to permit connection of the electrical pathways to associated electrical equipment (not explicitly shown).

Other types of energy may also be employed for use with the present disclosure, ultrasonic, microwave, optical, etc. As can be appreciated, different pin 66 and socket 70 arrangements, mechanical couplings, additional components and/or different electrical circuitry may be needed to provide one or more of the aforementioned alternate or different types of energy application to tissue.

In use, the reusable component 12 of the instrument 10 is sterilized by any conventional or appropriate sterilization techniques. Subsequently, the reusable component 12 may be mated with a new and sterile disposable component in a sterile operating field. The instrument 10 may then be employed in a surgical procedure wherein a surgeon or operator grips the stationary handle 34 (FIG. 2) of the reusable component and maneuvers and mechanically operates the end effector 24 with the mechanical actuators 36, 40, and 44 on the disposable portion 14. The end effector 24 may be electrically activated by operating the button 48. At the completion of the surgical procedure, the disposable component 14 may be separated from the reusable component 12 and discarded. The reusable portion may be re-sterilized for subsequent use. The cost per surgical procedure may be reduced by use of instrument 10 in this manner.

Figure 5:
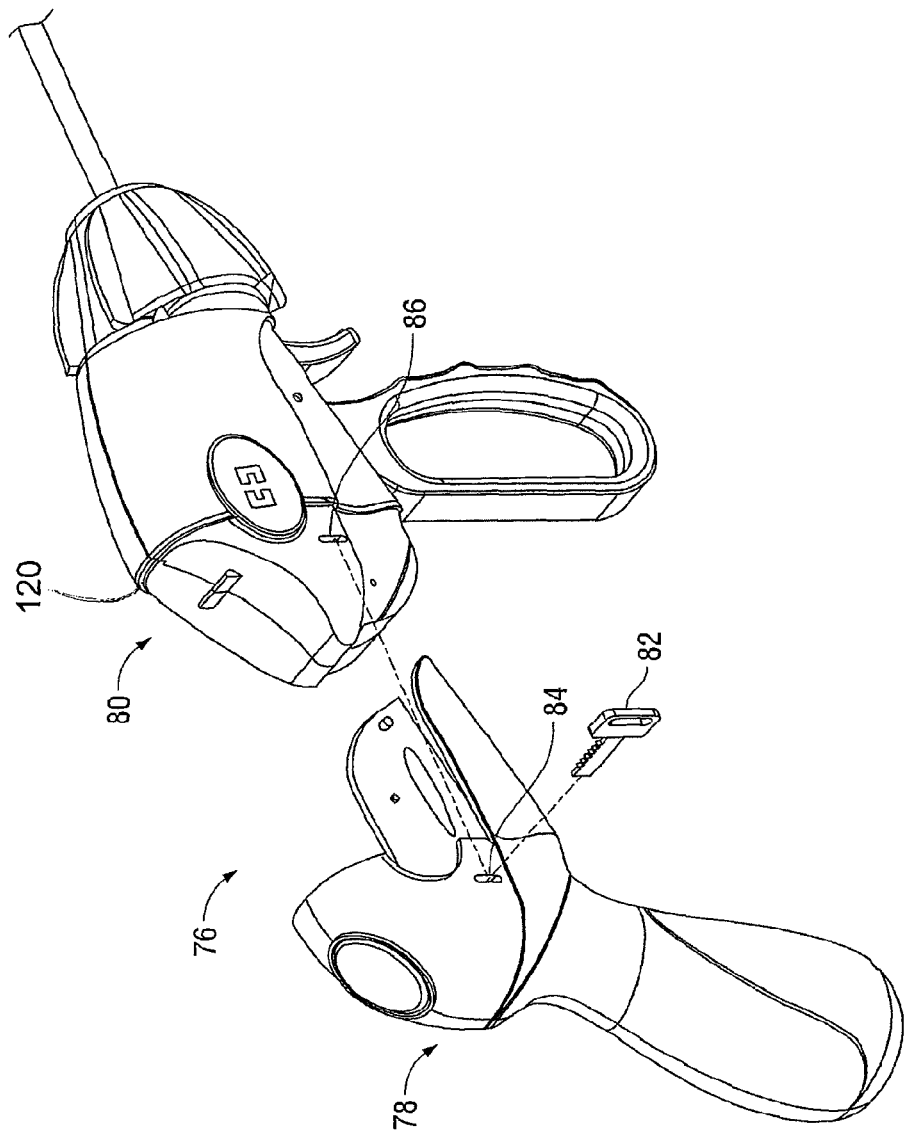
FIG. 5 is a partial, perspective view of an alternate embodiment of a surgical instrument including a key lock physical mating feature.

Referring now to FIG. 5, a an alternate embodiment of a surgical instrument 76 includes a reusable component 78 and a disposable component 80, which are engaged with one another in a substantially similar manner as the reusable and disposable components 12, 14 described above with reference to FIGS. 1 through 4. Additionally in instrument 76, a separate key or mechanical interface 82 is provided to complete the mechanical connection between the reusable and disposable components 78, 80. As the reusable and disposable components 78, 80 are approximated, keyholes 84 and 86 defined in the respective components 78, 80 are aligned. The key 82 may be inserted through the keyhole 84 in the reusable component 78 and into the keyhole 86 defined in the disposable component 80 to maintain the mechanical engagement between the components 78, 80.

The key 82 and keyholes 84, 86 may be associated with electronic sensors or circuits (not explicitly shown) that provide an indication to the generator 28 (or a control module associated with the generator 28) that a proper engagement between the components 78, 80 has been achieved. Sensors may include pressure sensors, proximity sensors, simple circuits, magnetic or ferromagnetic sensors, or any other type of sensor that may be utilized to provide feedback to the generator 28 (or a control module associated with the generator 28) that a proper mechanical or electromechanical connection between the reusable and disposable components 78, 80 has been achieved. Moreover, the sensors or circuit may be configured to provide feedback to the generator 28 (or a control module associated with the generator 28) during an electrosurgical procedure or provide a feedback test to ensure proper connection between components 78, 80 prior to activation.

Figure 6:
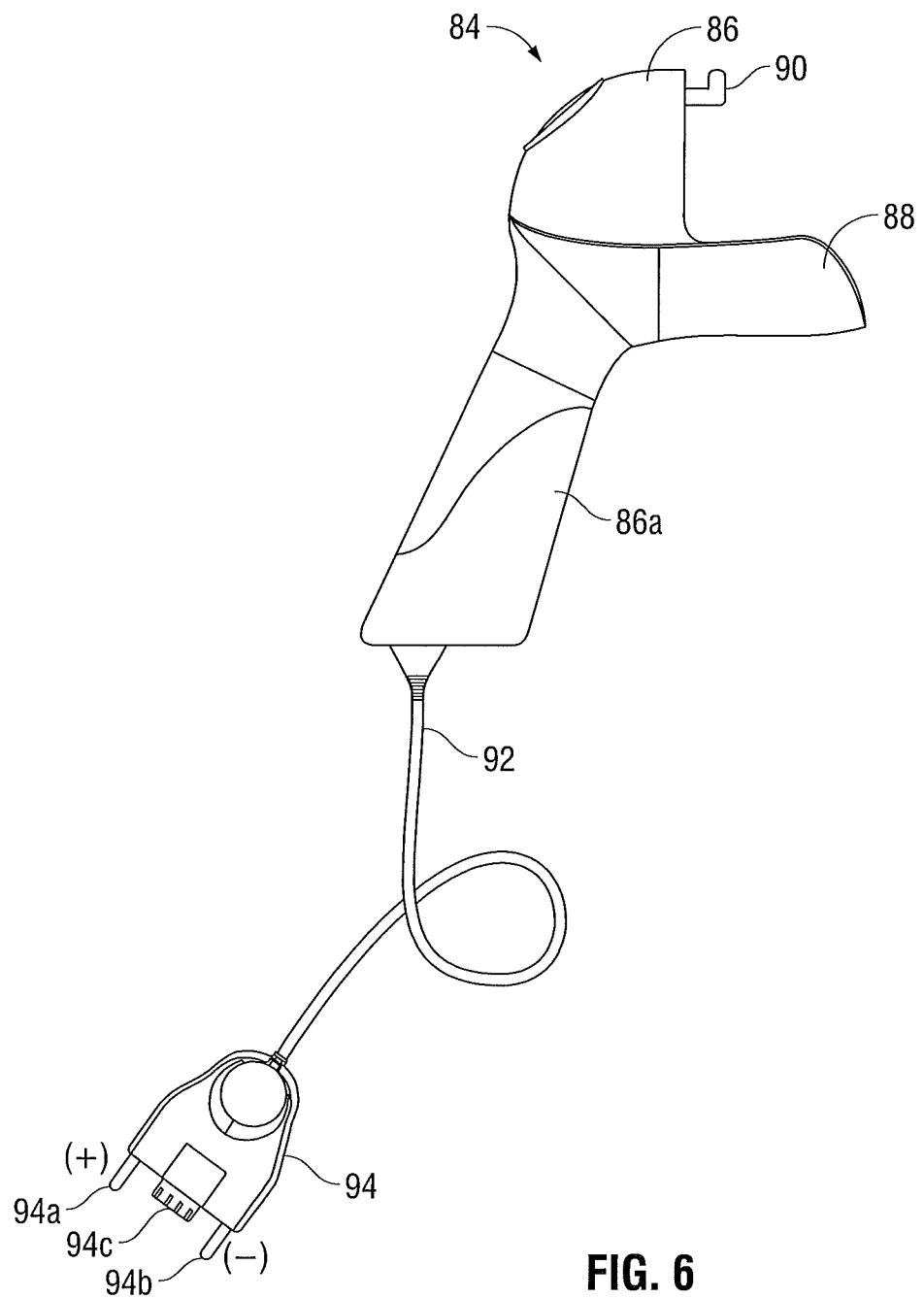
FIG. 6 is a right side view of an alternate embodiment of a reusable component of a surgical instrument depicting an electrical cable for coupling the reusable component to a source of electrosurgical energy.

Referring now to FIG. 6, an alternate embodiment of reusable component 84 includes a housing 86 defining a stationary handle 86a and guide arms 88. A hook 90 is provided in the housing 86 and may serve as a physical mating feature for engaging a lip (e.g., lip 120, see FIG. 5) in a disposable component, e.g., 14. Extending from the housing 86, a cable 92 provides a mechanism for electrically connecting the reusable component 84 to an external electrosurgical generator (not shown). The cable 92 includes a connector 94 for coupling the reusable component 84 to opposite terminals of the generator. The connector 94 includes two prong members 94a and 94b that are configured to mechanically and electrically connect the reusable component 84 to opposite terminals, e.g., positive or active (+) and negative or return (−) terminals associated with the generator. Thus, bipolar energy may be provided through reusable component 84. Alternatively, the reusable component 84 may be configured for receiving monopolar energy.

The connector 94 also includes a terminal array 94c. The terminal array 94c provides a connection mechanism for electrically coupling electrical signal transmission pathways associated with the reusable component 84 to the external electrosurgical generator (not explicitly shown). These electrical signal transmission pathways may communicate analog and/or digital signals between the reusable component and the electrosurgical instrument. In some embodiments, these electrical signal transmission pathways may extend through the reusable component 84 to an additional terminal array (not explicitly shown) that is adapted and arranged to electrically connect the signal transmission pathways to a disposable component whenever the hook 90 is engaged with a disposable component as described above.

In some embodiments, the reusable component 12 (or generator 28) and the disposable component 14 may be configured to recognize or identify one another and provide information relating to energy parameters, or the type of surgical procedure that is involved, e.g., monopolar, bipolar, ultrasonic, etc. Examples, of such reusable logic may include bar codes, Aztec Codes, optical codes and the like.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
    a disposable component including an end effector and a mechanical actuator disposed thereon, the mechanical actuator operable to induce mechanical movement of the end effector;
    a reusable component selectively separable from and engagable with the disposable component, the reusable component configured for providing electrosurgical energy to the disposable component when engaged with the disposable component;
    a physical mating feature provided on at least one of the disposable and reusable components, the physical mating feature configured to maintain engagement between the reusable and disposable components when the reusable and disposable components are engaged;
    an electrical mating feature provided on the disposable and reusable components configured to transmit electrical energy between the disposable and reusable components when the disposable and reusable components are engaged; and
    a keyhole formed in each of the disposable and reusable components, the keyholes configured for receipt of a key-like interface to maintain at least one of mechanical or electrical engagement of the reusable and disposable components during use thereof.

2. The surgical instrument according to claim 1, wherein the key-like interface is configured to provide indication to one of the reusable or disposable components that there is proper engagement therebetween.

3. The surgical instrument according to claim 1, wherein all mechanical motion resulting from operation of the mechanical actuator is contained within the disposable component.

4. The surgical instrument according to claim 1, wherein the physical mating feature includes a pair of contoured guide arms extending distally from the reusable component, the pair of contoured guide arms shaped to correspondingly mate with a pair of lateral indentations formed in an outer surface of the disposable component.

5. The surgical instrument according to claim 4, wherein each of the pair of contoured guide arms includes at least one boss extending inwardly from an interior surface thereof that are positioned to mate with corresponding cavities defined within the pair of lateral indentations of the disposable component.

6. The surgical instrument according to claim 1, wherein the physical mating feature includes at least one of lip and spring-loaded pin arrangements, tab and insert pins, screw or key features, magnetic and ferromagnetic components, or adhesives.

7. The surgical instrument according to claim 1, wherein the electrical mating feature includes a plurality of pins that extend from an interior surface of the reusable component that mate with a corresponding plurality of sockets defined in the housing of the disposable component.

8. The surgical instrument according to claim 7, further comprising a contact guide disposed on one of the reusable or disposable components and configured to facilitate alignment and engagement of the plurality of pins and corresponding plurality of sockets.

9. The surgical instrument according to claim 1, wherein the reusable component further includes a cable, the cable having a cable connector configured to electrically and mechanically connect to an electrosurgical energy source, the cable connector having one or more prongs and a terminal array, the terminal array being configured to couple electrical signal transmission pathways associated with the reusable component to the electrosurgical energy source.

10. A surgical instrument, comprising:
    a disposable component including;
        a housing;
        a mechanical actuator pivotably connected to the housing;
        an elongated shaft extending distally from the housing; and
        an end effector connected to the elongated shaft, wherein the mechanical actuator operably induces mechanical movement of the end effector;
    a reusable component including:
        a housing; and
        a stationary handle extending from the housing of the reusable component, wherein the housing of the reusable component is selectively separable from and engagable with the housing of the disposable component, the housing of the reusable component including an electrical switch disposed thereon and configured to allow selective application of electrosurgical energy to the end effector when the reusable component is engaged with the disposable component;
    at least one physical mating feature and at least one electrical mating feature provided on the housing of the reusable component each configured to engage the housing of the disposable component to maintain mechanical and electrical engagement therewith, wherein the physical mating feature includes a pair of contoured guide arms extending distally from the housing of the reusable component shaped to correspondingly mate with a pair of lateral indentations formed in an outer surface of the housing of the disposable component.

11. The surgical instrument according to claim 10, wherein each of the pair of contoured guide arms includes at least one boss extending inwardly from an interior surface thereof that is positioned to mate with corresponding cavities defined within the pair of lateral indentations of the housing of the disposable component.

12. The surgical instrument according to claim 10, wherein the disposable component further includes a knob rotatably connected to the housing of the disposable component.

13. The surgical instrument according to claim 10, wherein the mechanical actuator of the disposable component is a movable handle.

14. The surgical instrument according to claim 10, wherein the disposable component further includes a trigger pivotably connected to the housing of the disposable component.

15. A surgical instrument, comprising:
a disposable component including:
a housing having a proximal end;
a mechanical actuator pivotably connected to the housing;
an elongated shaft extending distally from the housing; and
an end effector connected to the elongated shaft, wherein the mechanical actuator operably induces mechanical movement of the end effector;
a reusable component including:
a housing defining a cavity therein configured for receipt of the proximal end of the housing of the disposable component; and
a stationary handle extending from the housing of the reusable component, wherein the housing of the reusable component is selectively separable from and engagable with the housing of the disposable component, the housing of the reusable component including an electrical switch disposed thereon and configured to allow selective application of electrosurgical energy to the end effector when the reusable component is engaged with the disposable component; and
at least one physical mating feature and at least one electrical mating feature provided on the housing of the reusable component each configured to engage the housing of the disposable component to maintain mechanical and electrical engagement therewith, wherein the at least one physical mating feature includes at least one of lip and spring-loaded pin arrangements, tab and insert pins, screw or key features, magnetic and ferromagnetic components, or adhesives.

16. The surgical instrument according to claim 15, wherein the at least one electrical mating feature includes a plurality of pins that extend from an interior surface of the housing of the reusable component that mate with a corresponding plurality of sockets defined in the housing of the disposable component.

17. The surgical instrument according to claim 16, further comprising a contact guide disposed on one of the housings of the reusable or disposable components and configured to facilitate alignment and engagement of the plurality of pins and corresponding plurality of sockets.

18. The surgical instrument according to claim 15, further comprising a a keyhole formed in each of the housings of the disposable and reusable components, the keyholes configured for receipt of a key-like interface to maintain at least one of mechanical or electrical engagement of the reusable and disposable components during use thereof.

19. The surgical instrument according to claim 18, wherein the key-like interface is configured to provide indication to a control module that the reusable and disposable components are properly engaged.

* * * * *